(12) United States Patent
Stewart et al.

(10) Patent No.: US 7,371,345 B2
(45) Date of Patent: May 13, 2008

(54) STERILIZATION OF MEDICAL ADHESIVE KITS

(75) Inventors: Ubonwan A. Stewart, Durham, NC (US); Melanie Vander Klok, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 909 days.

(21) Appl. No.: 10/325,912

(22) Filed: Dec. 23, 2002

(65) Prior Publication Data

US 2004/0120849 A1 Jun. 24, 2004

(51) Int. Cl.
*A61L 2/08* (2006.01)
(52) U.S. Cl. .......................... 422/22; 521/71; 522/173
(58) Field of Classification Search .................. 422/1, 422/22; 522/173; 521/71, 74, 77
See application file for complete search history.

(56) References Cited

U.S. PATENT DOCUMENTS

| | | | |
|---|---|---|---|
| 3,954,174 A | 5/1976 | Kraus | |
| 4,511,035 A * | 4/1985 | Alpern | 206/363 |
| 5,350,798 A | 9/1994 | Linden et al. | |
| 5,459,177 A | 10/1995 | Miyakoshi et al. | |
| 5,536,469 A | 7/1996 | Jonsson et al. | |
| 5,881,536 A | 3/1999 | Muller-Wille et al. | |
| 5,962,010 A | 10/1999 | Greff et al. | |
| 5,997,544 A | 12/1999 | Nies et al. | |
| 6,090,397 A | 7/2000 | Lee et al. | |
| 6,143,805 A | 11/2000 | Hickey et al. | |
| 6,248,800 B1 | 6/2001 | Greff et al. | |
| 6,833,408 B2 * | 12/2004 | Sehl et al. | 525/54.1 |
| 2002/0037310 A1 | 3/2002 | Jonn et al. | |
| 2002/0065336 A1 | 5/2002 | Hickey et al. | |

* cited by examiner

*Primary Examiner*—Gladys JP Corcoran
*Assistant Examiner*—Sean E. Conley

(57) ABSTRACT

Adhesive compositions, particularly medical adhesive compositions, often include several components that may react differently to different sterilization processes, particularly when combined with one another. The present invention is directed to methods of sterilizing different components or groups of components of a final adhesive composition. The different components or groups of components may be sterilized in separate containers before packaging the components or groups of components within a kit, and thereafter sterilizing the kit.

30 Claims, No Drawings

STERILIZATION OF MEDICAL ADHESIVE KITS

BACKGROUND OF THE INVENTION

1. Field of Invention

The present invention is directed to the sterilization of liquid and gel or gel-like compositions that are useful as biomedical adhesives and sealants and particularly to sterilization of kits of such liquid and gel or gel-like compositions. In particular, the present invention relates to the application of separate sterilization processes to discrete components of the liquid and gel or gel-like compositions, and kits containing the liquid and gel or gel-like compositions assembled from components treated by the separate sterilization processes.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

When such adhesive compositions are desired to be used in the medical arts, it is often required, or at least preferred, that the adhesive composition be sterile. Likewise, it is often required, or at least preferred, that the applicators used to apply the adhesive composition, also be sterile. A variety of sterilization methods are generally used to sterilize monomeric and polymeric compositions as well as the packaging of such kits. These methods include chemical, physical, and irradiation methods. Examples of chemical methods include exposure to ethylene oxide or hydrogen peroxide vapor. Physical methods of sterilization may include, for example, sterilization by dry or moist heat. Gamma irradiation, electron beam (e-beam) irradiation, and microwave irradiation are some common examples of irradiation methods. Aseptic filling may also be used to provide sterile compositions.

U.S. Pat. No. 6,143,805 to Hickey et al. discloses a method for sterilizing a liquid adhesive composition, and in particular embodiments an α-cyanoacrylate adhesive composition, by e-beam irradiation while it is enclosed in a container. After the container containing the liquid adhesive composition is sterilized by e-beam radiation, the container may be further subjected to a second sterilization step or process. The patent also discloses that the container may be placed in a kit with other components that need to be sterilized, after which the entire kit may then be sterilized. In addition to e-beam irradiation, the entire kit may be sterilized by chemical, physical or other techniques such as microwave irradiation or γ-irradiation.

U.S. Pat. No. 6,248,800 discloses a method for sterilizing a polymerizable cyanoacrylate ester composition in a shipping element comprising multiple individual packages of cyanoacrylate compositions. A packaging element, such as an ampoule made of glass, polyalkylene based polymers, metal foils or polyolefins, is filled with a cyanoacrylate ester composition comprising a polymerizable cyanoacrylate ester. These filled packaging elements are then placed into a shipping element and exposed to a sufficient dosage of e-beam radiation maintained at an initial fluence of at least 2 µCurie/cm$^2$ to sterilize both the packaging elements and the cyanoacrylate ester composition therein without gelling the composition. The average bulk density of the materials comprising all of the packaging elements is less than about 0.2 gm/cm$^3$. In another embodiment, the patent discloses first exposing the empty ampoule to a gas stream comprising a sufficient amount of ethylene oxide to reduce the level of bioburden on the ampoule, before filling the ampoule with the cyanoacrylate adhesive.

U.S. Pat. No. 5,997,544 discloses a process for producing sterile-packed bone cement, comprising providing a first and a second container connected through a sealing device between the containers. The first container contains a polymer powder and the second contains a monomer. The containers are sterilized by introducing a sterilizing gas, such as ethylene oxide, into the containers via sterile filters attached to both containers.

U.S. Pat. No. 3,954,174 discloses a unitary two-compartment package for sterile surgical articles. The package comprises two separate and sealed containers that are joined to each other. The containers are defined by walls of sheet material permeable to a sterilizing agent. The disclosed package permits the packaging of surgical articles that may require diverse means of sterilization in a single package. For example, a germicidal liquid in one container may be sterilized by exposure to cobalt radiation, while surgical drapes or applications in the second container are sterilized via ethylene oxide gas. Once the individual packages have been sterilized, they are joined to form the described package. The reference discloses the package itself as well as the separate sterilization of diverse surgical articles.

Despite the increasing use of cyanoacrylate adhesives in medical and non-medical applications, the need exists for new and improved liquid and gel or gel-like adhesive compositions, and kits containing such compositions that enable their use in still further and varied applications. At the same time, however, as the formulations of the liquid and gel or gel-like adhesive compositions change to adapt to such further and varied applications, new sterilization techniques are required in order to provide the desired sterilization of the kit and all of its components.

SUMMARY OF THE INVENTION

The present invention is directed to such new and improved liquid and gel or gel-like adhesive compositions, and processes for effectively sterilizing such compositions. More particularly, the present invention is directed to processes for effectively sterilizing liquid and gel or gel-like adhesive compositions, and kits of such compositions, which otherwise are not amenable to conventional single-step sterilization processes.

In particular, the present inventors have discovered that as the formulations of the liquid and gel or gel-like adhesive compositions are varied, such changes have presented significant challenges to sterilization of the compositions and kits. As used herein, the term "gel" refers to a composition that has a viscosity high enough such that the composition has the consistency of jelly. The term "gel-like" refers to a composition in which the viscosity of the composition is such that the composition is more liquid than a gel. A gel-like composition may have, for example, the consistency of a very thick syrup. It has now been discovered that some adhesive compositions cannot be fully sterilized as a single composition, because various of the component materials react adversely to the sterilization process. For example, adhesive compositions have been prepared to include a plasticizer, which provides desirable elasticity and tensile properties to a polymeric film or article formed from the composition. However, some plasticizer materials in some amounts have been found to react adversely to the even moderate level of irradiation necessary to sterilize the adhesive composition. The irradiation can cause the plasticizers to at least partially degrade, often into byproducts that in turn act as initiators or stabilizers for the liquid and gel or gel-like adhesive. The result is that the sterilization process renders the product unusable. Any initiators created as degradation byproducts can cause the composition to prematurely polymerize. On the other hand, any stabilizers created as degradation byproducts can cause the composition to become "more stable" and more difficult to polymerize completely.

To overcome this problem, the present inventors conducted extensive investigation into alternative ways to sterilize the liquid and gel or gel-like adhesive compositions, and kits containing such compositions. The present inventors have discovered suitable sterilization processes that provide not only a sterile liquid and gel or gel-like adhesive composition and kits, but such sterile compositions and kits that retain their usefulness for a sufficient time (i.e., a useful shelf-life) for their desired purposes.

One such process is to sterilize individual components of the composition and/or kit separately from other components of the kit. In this method, components of the composition or kit that can withstand higher or longer sterilization processing are sterilized first. The first components are then combined with the remaining components of the composition or kit, and the combined composition or kit is then subjected to terminal sterilization. In an alternate method, separate components of the composition, or kit, are sterilized separately by respective suitable sterilization processes. The separate components are then combined together into a kit, which is then subjected to terminal sterilization, for example, to sterilize the kit-packaging element itself.

As used herein, the phrase "terminally sterilize" or variants thereof refers to a process by which a product is sterilized in its final container. For example, a kit may consist of several components. Each component may be individually sterilized by an appropriate means of sterilization. Once all the components are packaged into a kit (in a final container), the kit can be subjected to terminal sterilization where the outer surface of each component will be sterilized. As another example, a first container with solid materials may be irradiated (e-beam) at an initial dose of 10 kGy. This container and the second container (containing adhesive composition) are then assembled into a kit, which is then irradiated (terminal sterilization) at the dose of 15 kGy rendering the outer surfaces of both containers and their contents sterile.

The present invention is thus directed to methods of sterilizing different components or groups of components of a final adhesive composition. The different components or groups of components may be sterilized in separate containers before packaging the components or groups of components within a kit, and thereafter terminally sterilizing the kit. Different sterilization techniques may be used as determined by the compatibility of each adhesive component and/or its container.

Thus, a kit may comprise a package containing a mixture of plasticizer, thickening agent, radiopaque agent and initiator sterilized by irradiation. The irradiated package may then be combined in the kit with a second package containing a liquid or gel or gel-like adhesive, such as cyanoacrylate monomer adhesive. The entire kit could then be irradiated a second time, at a dose sufficient to terminally sterilize the kit. Thus, the adhesive is only subjected to a single dose, while the other package is subjected to both doses, providing a relatively higher irradiation dose.

A combination of different methods may be used to sterilize the components of a kit. A package containing a mixture of adhesive (e.g., cyanoacrylate) and plasticizer can be sterilized, for example, using dry heat, while a second package containing a mixture of thickening agent, radiopaque agent and initiator may be sterilized, for example, by irradiation. The two packages may then be placed together in a kit that is in turn chemically sterilized such as by ethylene oxide or hydrogen peroxide vapor. Other acceptable component combinations and sterilization techniques may be used as appropriate.

DETAILED DESCRIPTION OF PREFERRED EMBODIMENTS

The process of the invention comprises separately sterilizing different components or groups of components that, when mixed together, form an adhesive composition. Thus, for example, an adhesive composition that would otherwise contain various components, such as polymerizable monomer, stabilizing agent, thickener, plasticizer, radiopaque agent, colorant, flavorant, medicament, fibrous reinforcement agent, thixotropic agent, natural or synthetic rubber, pH modifier, formaldehyde scavenger, preservative, and/or the like, is separated by components into at least two separate compositions for separate sterilization. The separated components may be combined into a kit, either after the separate components are sterilized, or between sterilization steps.

Adhesive compositions, particularly medical adhesive compositions, often include several components that may react differently to different sterilization processes, particularly when combined with one another. For example, as described briefly above, it is often desirable to add one or more plasticizing agents into a polymerizable monomer adhesive composition. However, the present inventors have discovered that different plasticizers, and particularly when used in different amounts, react differently to sterilization processing. By way of example only, experiments were conducted using isopropyl myristate or acetyl tri-n-butyl citrate as plasticizers. When isopropyl myristate was used, the plasticizer could be mixed with the monomer composition, and the entire composition could be sterilized by e-beam irradiation as a single composition and without any adverse effects. However, when acetyl tri-n-butyl citrate was used as a plasticizer, particularly in larger amounts to provide its desired effect, it was discovered that the e-beam irradiation caused the plasticizer to degrade into degradation products that interfered with the complete polymerization of the composition when initiated, rendering the product useless.

The present inventors overcame these problems by developing new sterilization processes for the adhesive compositions and kits thereof. To avoid subjecting the components to a sterilization process with which the component or groups of components of a final adhesive composition may be incompatible, the different components or groups of components may be separately sterilized. Once sterilized, or at a suitable point in the sterilization process, the separate components or groups of components may be packaged in separate containers within a kit. Thereafter, the entire kit itself may be subjected to further sterilization, if desired.

As used herein, "compatible," as referring to a material being compatible with the adhesive formulation or another component, means that the material does not cause premature polymerization of the adhesive composition, or does not otherwise render the adhesive composition unusable for its intended purpose. Likewise, "incompatible," as referring to a material being incompatible with the adhesive formulation or another component, means that the material does cause premature polymerization of the adhesive composition, or otherwise renders the adhesive composition unusable for its intended purpose.

As a non-limiting example only, in a first embodiment of the present invention, the adhesive composition generally includes a polymerizable monomer, plasticizer, thickening agent, and radiopaque agent, in addition to such materials as stabilizers and optional colorant. The adhesive composition is generally activated, i.e., initiated, by contact with a separate initiator. However, because the polymerizable monomer cannot withstand as much irradiation sterilization as the other components, the various components of the composition are divided into two separate groups for sterilization. In this embodiment, the kit may include a mixture of plasticizer, thickening agent, radiopaque agent and initiator packaged together, which is sterilized by irradiation (e.g., e-beam or γ irradiation) at a relatively low dose (e.g., 5-15 kGy). A package or container containing the irradiated composition could then be combined in a kit with a second package containing an adhesive, such as cyanoacrylate monomer adhesive. Once combined, both components of the kit may then be sterilized again, using the same or a different sterilization dose. Thus, the adhesive is only subjected to the second low dose, while the other package or container is subjected to both doses, providing a relatively higher level of irradiation dose.

Alternatively, in a second embodiment of the present invention, where the plasticizer is degraded by irradiation sterilization to render the formulation unsuitable for its intended purpose, the plasticizer can be packaged with the polymerizable monomer for sterilization processing by a method other than irradiation sterilization, and other components can be sterilized separately. In this embodiment, a package or container containing a mixture of polymerizable adhesive (e.g., cyanoacrylate) and plasticizer can be sterilized with dry heat, while a package containing a mixture of thickening agent, radiopaque agent and initiator can be sterilized with e-beam or γ-irradiation. The two packages are then placed together in a kit that is in turn sterilized with ethylene oxide gas or hydrogen peroxide vapor. Other acceptable component combinations and sterilization techniques may also be used in accordance with the invention.

Accordingly, in embodiments of the present invention, the respective components of an adhesive composition or kit are first considered to determine whether and to what extent they should be separated in order to perform adequate sterilization of all of the components of the composition or kit. Such consideration can be based, for example, on known chemical interaction, experimental observations, product packaging considerations, end use considerations, and the like.

Known chemical interactions provide the first consideration in determining any separation of composition components. For example, as is known in the art, a suitable initiator can be selected to cause polymerization of the adhesive composition. As used herein, an "initiator" encompasses not only a compound that causes initiation of polymerization of monomer species in the adhesive composition, but also compounds that cause and/or accelerate polymerization or cross-linking of the adhesive composition. When such an initiator is to be used, the initiator should be kept separate from at least the polymerizable species of the adhesive composition until the desired time of use. Other compounds, known to cause adverse reactions with the polymerizable species of the adhesive composition, should also generally be maintained separate from the polymerizable species. Likewise, it is also known that stabilizers, or polymerization inhibitors, can be used to prolong the monomeric form of the adhesive composition. In order for such compounds to serve their intended purpose, it is generally desirable to maintain such stabilizers together with the polymerizable species of the adhesive composition.

Experimental observations can also be used to determine any separation of composition components. For example, as described above, experiments have shown that some plasticizers, such as acetyl tri-n-butyl citrate, produce degradation products upon e-beam irradiation, which degradation products cause the adhesive composition to become "more stable" and more difficult to polymerize completely. Further, such interactions may be apparent based on different product formulations and/or different sterilization processes. Such experimental observations can thus also indicate a need to separate one or more components from other components of the adhesive composition.

Still further considerations for assessing any need or desire to separate composition components can be product packaging considerations and end use considerations. For example, in embodiments, it may be desirable to separate one or more components from the remainder of the adhesive composition, to address packaging concerns such as preferences in terms of containers that are used or the like. Likewise, in embodiments, it may be desirable to separate one or more components from the remainder of the adhesive composition, to provide for different uses of the composition, or to allow the end-user to tailor the mixing proportions of different components to meet particular needs.

In one embodiment of the present invention, the materials are separated based on incompatibility of one component with another component of the composition. That is, where a mixture of the two components together would have an adverse effect on the composition, even in the absence of sterilization, the respective components should be separated.

In another embodiment of the present invention, the materials are separated based on incompatibility of one component with another component of the composition that arises only due to the sterilization processing. That is, where a mixture of the two components together would otherwise form an acceptable composition, but the mixture would experience an adverse effect as a result of sterilization, the respective components should be separated and sterilized separately and maintained separate in the kit.

In yet a further embodiment of the present invention, the materials are separated regardless of their compatibility in the composition, both before and after sterilization. That is, in embodiments, it may be desirable to separate two components of the composition although the components would otherwise be compatible with each other, and with other components of the adhesive composition that may be present together, regardless of the selected sterilization procedures.

After a separation of the components is determined, suitable packaging for each of the respective components can be determined. For example, suitable packaging can include ampoules, bottles, vials, tubes, pouches, envelopes, sachets, syringes, pipettes, and the like. For example, liquid components of the composition or kit can be packaged in suitable containers, such as bottles, vials, tubes, pouches, envelopes, sachets syringes, pipettes, or the like, that provide any necessary or desirable barrier properties. Likewise, applicators or other solid materials of the composition or kit can be packaged in suitable containers, such as bottles, vials, tubes, pouches, envelopes, sachets, and the like, although in the case of applicators or larger objects, simple envelopes or pouches may be suitable and preferred. Alternatively, as long as the kit packaging is suitably designed, one or more of the separate components of the composition or kit can be packaged loose in the kit, such as in a compartment, well, dimple, recess, or the like. Other variations will be apparent based on the present disclosure.

Once desired separation and packaging of the components is determined, an appropriate sterilization process sequence can be selected. The sterilization process sequence, as desired or as necessary, can include two or more different sterilization processes, which can be conducted on the respective composition components in series and/or in parallel. That is, when conducted in parallel, at least two separate components of the adhesive composition or kit are sterilized separated or apart from each other, prior to being placed into a kit. When conducted in series, one of at least two separate components of the adhesive composition or kit is sterilized separated or apart from the other(s); the sterilized component is then placed into a kit with the remaining component(s), and a successive sterilization step is conducted on the kit. Combinations of these approaches can of course be used, especially where the kit includes three or more separate parts (i.e., multiple separated composition components, one or more applicators, and the like).

Although the present discussion focuses on the adhesive composition being separated into two separate sub-units, the present invention is in no way limited to such embodiments. Rather, the processes of the present invention can be equally and desirably utilized where a kit of three, four, five, six or more separate parts are included. Thus, for example, the processes of the present invention can be used to separately sterilize three or more components of an adhesive composition; to separately sterilize two components of an adhesive composition and a separate applicator; to separately sterilize an adhesive composition, a separate applicator, and a separate other component of the kit; and the like. Such modifications of the process of the present invention will be apparent to one skilled in the art, and are encompassed by the present invention. When such modifications are employed, combinations of the above-described parallel and serial processing are likewise applicable.

For sterilizing the various components of the kit, any of the suitable sterilization processes can be used. Thus, for example, suitable sterilization processes include, but are not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, $\gamma$-irradiation, e-beam irradiation, and microwave irradiation. A preferred method is e-beam irradiation, as described in U.S. Pat. No. 6,143,805, the entire disclosure of which is incorporated herein by reference.

According to the present invention, the preferred selected sterilization process can also vary depending on the particular component(s) being sterilized. Thus, for example, e-beam or dry heat irradiation may be preferred for sterilizing the polymerizable monomer, optionally in combination with other composition components, and e-beam for other solid materials. However, where applicators or other parts of the kit, or the kit packaging itself, are to be sterilized, chemical methods such as exposure to ethylene oxide or hydrogen peroxide vapor may be preferred.

Furthermore, in embodiments of the present invention, it may be desirable to conduct a sterilization process on one or more of the containers of the kit, prior to individual adhesive composition components being introduced into the containers. Thus, for example, where solid materials are to be stored in respective vials, syringes, bottles, or the like, it may be desirable to expose the empty containers or the empty kit packaging element to a sterilization process such as ethylene oxide or hydrogen peroxide gas, to reduce the bioburden of the containers. Of course, any other suitable sterilization process can also be used.

In selecting the sterilization processes, an important consideration is the effect, if any, that the individual and overall sterilization processes have on the respective composition components. For example, it is known that excessive sterilization exposure, particularly to irradiation, can cause polymerization of the polymerizable monomer. Thus, for example, where multiple sterilization cycles are used in series, the multiple cycles should be selected such that either the total sterilization dose is within an acceptable range, or such that the polymerizable monomer is not exposed to all of the successive processes. Similar concerns may also apply to other components in the adhesive composition and/or kit.

Thus, for example, care must be exercised when sterilizing the polymerizable adhesive composition, particularly by e-beam irradiation. When the polymerizable adhesive composition is to be exposed to only one irradiation process, the irradiation can be in a suitable amount of, for example, from about 10 to about 50 kGy, preferably about 15 to about 30 kGy. However, when the polymerizable monomer is to be exposed to two successive irradiation processes, the total irradiation from both processes should be controlled to be in the above-described amounts. Thus, a first irradiation process could deliver a dose of from about 5 to about 25 kGy, preferably about 8 to about 15 kGy, and the second irradiation process could deliver an additional dose of from about 5 to about 25 kGy, preferably about 8 to about 15 kGy. Similar concerns, and dosage ranges, apply to the use of $\gamma$-irradiation, or to combinations of $\gamma$ and e-beam irradiation.

Regardless of the sterilization methods used, the respective components of the kit, and preferably the entire kit and its contents, should be sterile. By "sterile" herein is meant that the composition or component is free from viable microorganisms. In preferred embodiments of the present invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$.

As a result of the sterilization processes, there is preferably substantially no initiation of polymerization of the liquid or gel or gel-like adhesive composition. That is, the sterilization processes preferably do not cause polymerization of the composition, which would render the composition unusable for its intended purpose.

As described briefly above, the kits of the present invention can include one or more containers of material, such as components of an adhesive composition, or one or more compartments containing such materials, and optionally one or more applicators or other parts. Although not limited to any particular construction, the kit container (also referred to as a kit packaging element) itself can be any suitable container, including but not limited to a bottle, jar, carton, box, or the like. The kit container can be formed of any suitable material including, but not limited to, paper, cardboard, plastic, metal, glass, or the like. Suitable kit container designs are disclosed in, for example, U.S. patent applications Ser. No. 09/145,200, filed Sep. 1, 1998, Ser. No. 09/385,030, filed Aug. 30, 1999, Ser. No. 09/987,116, filed Nov. 13, 2001, and Ser. No. 09/559,651, filed Apr. 28, 2000, the entire disclosures of which are incorporated herein by reference.

The kits can be particularly adapted, in terms of their construction and/or contents, for a wide range of medical procedures. For example, the kits can be used for apposing surgically incised or traumatically lacerated tissues; retarding blood flow from wounds; dressing burns; dressing skin or other superficial or surface wounds (such as abrasions, chaffed or raw skin, ulceration and/or stomatitis); hernia repair; meniscus repair; and aiding repair and re-growth of living tissue. One particular example of a surgical kit that can be prepared includes a kit whose construction and contents is particularly adapted for use in lung volume reduction procedures. Such lung volume reduction procedures, and compositions and kits useful therefor, are described, for example, in U.S. Provisional Patent Application No. 60/231,569, filed Sep. 11, 2000, and U.S. patent application Ser. No. 09/949,644, filed Sep. 12, 2001, the entire disclosures of which are incorporated herein by reference.

Furthermore, in embodiments of the present invention, the kits and contents can be used in non-medical procedures, including but not limited to industrial and home applications, for example in bonding rubbers, plastics, wood, composites, fabrics, and other natural and synthetic materials. Although sterilization may not be required for such applications, sterilization may still be preferred to retard bacterial growth and the like, and/or in environments where increased sterility is desired.

The composition in embodiments of the invention is preferably a monomeric adhesive composition. The monomer (including prepolymeric) adhesive composition may include one or more polymerizable monomers. In embodiments, the monomer is a 1,1-disubstituted ethylene monomer, e.g., an α-cyanoacrylate. Preferred monomer compositions of the present invention and polymers formed therefrom are useful as tissue adhesives, sealants for preventing bleeding or for covering open wounds, and in other biomedical applications. They find uses in, for example, apposing surgically incised or traumatically lacerated tissues; retarding blood flow from wounds; drug delivery; dressing burns; and aiding repair and regrowth of living tissue.

Monomers that may be used in this invention are readily polymerizable, e.g., anionically polymerizable or free radical polymerizable to form polymers. Such monomers include those that form polymers, which may, but do not need to, biodegrade. Reference is made, for example to U.S. Pat. Nos. 5,328,687, 6,183,593 and 5,928,611, U.S. patent application Ser. No. 09/430,177, filed on Oct. 29, 1999, which are hereby incorporated by reference in their entirety. Useful 1,1-disubstituted ethylene monomers include, but are not limited to, monomers of the formula:

$$HRC=CXY \qquad (I)$$

wherein X and Y are each strong electron withdrawing groups, and R is H, —CH=CH$_2$ or, provided that X and Y are both cyano groups, a C$_1$-C$_4$ alkyl group. Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 3 to about 8 carbon atoms.

The α-cyanoacrylates of the present invention can be prepared according to methods known in the art. U.S. Pat. Nos. 2,721,858, 3,254,111, 3,995,641, and 4,364,876, each of which is hereby incorporated in its entirety by reference herein, disclose methods for preparing α-cyanoacrylates.

Preferred α-cyanoacrylate monomers used in this invention include methyl cyanoacrylate, ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, or dodecylcyanoacrylate.

Suitable cyanoacrylates for use in the present invention also include, but are not limited to, alkyl ester cyanoacrylate monomers such as those having the formula

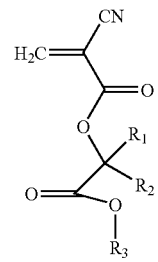

wherein R$_1$ and R$_2$ are, independently H, a straight, branched or cyclic alkyl, or are combined together in a cyclic alkyl group, and R$_3$ is a straight, branched or cyclic alkyl group. Preferably, R$_1$ is H or a C$_1$, C$_2$ or C$_3$ alkyl group, such as methyl or ethyl; R$_2$ is H or a C$_1$, C$_2$ or C$_3$ alkyl group, such as methyl or ethyl; and R$_3$ is a C$_1$-C$_{16}$ alkyl group, more preferably a C$_1$-C$_{10}$ alkyl group, such as methyl, ethyl, propyl, butyl, pentyl, hexyl, heptyl, octyl, nonyl or decyl, and even more preferably a C$_2$, C$_3$ or C$_4$ alkyl group. Such alkyl ester cyanoacrylates and other suitable monomers are disclosed in, for example, U.S. patent applications Ser. No. 09/630,437, filed Aug. 2, 2000, and Ser. No. 09/919,877, filed Aug. 2, 2001, the entire disclosures of which are incorporated herein by reference.

Examples of preferred alkyl ester cyanoacrylates include, but are not limited to, butyl lactoyl cyanoacrylate (BLCA), butyl glycoloyl cyanoacrylate (BGCA), ethyl lactoyl cyanoacrylate (ELCA), and ethyl glycoloyl cyanoacrylate (EGCA). BLCA may be represented by the above formula, wherein $R_1$ is H, $R_2$ is methyl and $R_3$ is butyl. BGCA may be represented by the above formula, wherein $R_1$ is H, $R_2$ is H and $R_3$ is butyl. ELCA may be represented by the above formula, wherein $R_1$ is H, $R_2$ is methyl and $R_3$ is ethyl. EGCA may be represented by the above formula, wherein $R_1$ is H, $R_2$ is H and $R_3$ is ethyl.

The compositions of the present invention may include at least one plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to isopropyl myristate, isopropyl palmitate, tributyl citrate, acetyl tri-n-butyl citrate (ATBC), polymethylmethacrylate, polydimethylsiloxane, polyester glutarates; polyester adipates; polyester sebacates; and others as listed in U.S. Pat. No. 6,183,593, the disclosure of which is incorporated in its entirety by reference herein.

Other compositions are exemplified by U.S. Pat. Nos. 5,259,835, 5,328,687, 5,981,621, 6,143,352, 6,010,714, 6,217,603, and 5,928,611 and U.S. patent application Ser. No. 08/909,845, all incorporated by reference herein in their entirety.

The composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. Nos. 4,720,513and 6,310,166, the disclosures of which are hereby incorporated in their entireties by reference herein. Fumed silica, such as that described in U.S. Pat. Nos. 4,477,607, 4,533,422, and RE 32,889, may also be used as the thixotropic agent in the composition.

The composition may optionally also include thickeners. Suitable thickeners may include poly (2-ethylhexyl methacrylate), poly(2-ethylhexyl acrylate) and others as listed in U.S. Pat. No. 6,183,593, the disclosure of which is incorporated by reference herein in its entirety.

The composition may also optionally include at least one natural or synthetic rubber to impart impact resistance. The skilled artisan would know of such suitable rubbers. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The composition may also optionally include a radiopaque agent to make the polymerized material visible upon x-ray examination. Suitable radiopaque agents may include, but are not limited to, tantalum powder, iodine-containing compounds including ethiodized oil, and barium sulfate.

The composition may optionally also include one or more stabilizers, preferably both at least one anionic vapor phase stabilizer and at least one anionic liquid phase stabilizer. These stabilizing agents may inhibit premature polymerization. Suitable stabilizers may include those listed in U.S. Pat. No. 6,183,593, the disclosure of which is incorporated by reference herein in its entirety. Other suitable stabilizers, which have additional functions in the composition, are disclosed in U.S. patent applications Ser. No. 09/657,913, filed Sep. 8, 2000, and Ser. No. 09/964,415, filed Sep. 28, 2001, the entire disclosures of which are incorporated herein by reference.

The stability, and thus the shelf-life, of some monomeric adhesive compositions can be further enhanced and extended through careful regulation of the packaging. Treated (e.g., fluorinated polymer) packaging such as that disclosed in copending U.S. patent application Ser. No. 09/430,289, filed Oct. 29, 1999, which is hereby incorporated by reference herein in its entirety, is preferred and may reduce the amount of stabilizer that is combined into the composition. Other suitable container constructions are disclosed, for example, in U.S. patent application Ser. No. 09/657,913, the entire disclosure of which is incorporated herein by reference.

The compositions may also include pH modifiers to control the rate of degradation of the resulting polymer, as disclosed in U.S. Pat. No. 6,143,352, the entire disclosure of which is hereby incorporated by reference herein in its entirety.

Compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al., which are hereby incorporated herein by reference in their entireties.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The compositions of this invention may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety.

The polymerizable compositions useful in the present invention may also further contain one or more medicaments, preferably one or more non-antioxidant medicaments. Suitable medicaments include, but are not limited to, antibiotics, antimicrobials, antiseptics, bacteriocins, bacteriostats, disinfectants, steroids, anesthetics, antifungal agents, anti-inflammatory agents (other than the dual function stabilizers of the present invention), antibacterial agents, antiviral agents, antitumor agents, growth promoting substances, antioxidants (other than the dual function stabilizers of the present invention), or mixtures thereof. Suitable specific medicaments are disclosed in, for example, U.S. patent application Ser. No. 09/430,177, filed Oct. 29, 1999, the entire disclosure of which is incorporated herein by reference.

The polymerizable compositions useful in the present invention may also further contain one or more preservatives. Suitable preservatives, and methods for selecting them and incorporating them into adhesive compositions, are disclosed in U.S. patent application Ser. No. 09/430,180, the entire disclosure of which is incorporated herein by reference. Such preservatives can be in addition to any antifungal agent that may or may not be added to the composition, as described above. Such preservatives can be included irrespective of whether the composition and containers are sterilized.

In embodiments of the present invention, the composition and/or its applicator may contain materials such as a polymerization initiator, accelerator, rate-modifier, and/or cross-linking agent for initiating polymerization and/or cross-linking of the polymerizable monomer material. Suitable materials and applicators and packaging systems are disclosed in U.S. Pat. Nos. 5,928,611, 6,352,704 and U.S. patent applications Ser. Nos. 09/430,177, 09/430,176, 09/430,289, 09/430,290, and 09/430,180 filed Oct. 29, 1999; Ser. No. 09/385,030 filed Aug. 30, 1999; and Ser. No. 09/176,889 filed Oct. 22, 1998; the entire disclosures of which are incorporated herein by reference.

EXAMPLES

The following examples illustrate specific embodiments of the invention. These examples are intended to be illustrative only, and the invention is not limited to the materials, conditions, or process parameters set forth in the Examples.

Example 1

A finished adhesive composition consisting of components of stabilized monomer (2-octyl cyanoacrylate), plasticizer (isopropyl myristate), thixotropic agent (fumed silica), and radiopaque agent (tantalum powder) is desired. The composition is to be initiated using benzalkonium chloride or butyrylcholine chloride. The components are divided into two elements. Element one contains the stabilized monomer packaged in a fluorinated high-density polyethylene bottle. Element two contains the plasticizer, thixotropic agent, radiopaque agent, and an amount of initiator to provide the desired setting time. The components of element two are first mixed to form a homogeneous gel-like material. The element two composition is then packaged into a syringe (glass or plastic).

Element two is sterilized first using an e-beam or γ-irradiation dose of 5 to 15 kGy. This dose reduces the bioburden in the product. To form the kit, non-sterile element one is added to the sterilized element two in a foil pouch. The foil pouch is sealed. The two elements in the foil pouch are exposed to an e-beam irradiation dose of 15 kGy. Element two has then been exposed to approximately 30 kGy. Element one has been exposed to the single dose of 15 kGy. The sterilization steps are sequential.

When it is time to use the composition, element one and element two are mixed. The polymerization time ("working time") is related to the initiator level. The flexibility of the resulting polymer is related to the amount of plasticizer.

The result is a medical procedure kit that includes compositions 1 and 2, which are both sterilized and substantially retain their original properties in terms of viscosity and appearance. The compositions can be mixed and subsequently applied to a surface. Mixing of the compositions 1 and 2 initiates polymerization of the monomer, providing a polymer film or plug.

Example 2

The same composition as described in Example 1 is desired. The components are divided into two elements. Element one contains the stabilized monomer and the plasticizer in a fluorinated high-density polyethylene bottle. Element two contains the thixotropic agent, radiopaque agent, and an amount of initiator to provide the desired setting time. The components of element two may be mixed together to form a homogeneously distributed powder (all components are solids), or the components may be added sequentially to the packaging container. The element two components are packaged into a syringe.

The sterilization steps described in Example 1 are repeated.

If the plasticizer level and initiator amount are the same for example two as in example one, the polymerization time and the flexibility of the resulting polymer will be very similar to example one.

Example 3

A finished adhesive composition consisting of components of stabilized monomer (2-octyl cyanoacrylate), plasticizer (acetyl tri-n-butyl citrate, ATBC), thixotropic agent (fumed silica), and radiopaque agent (tantalum powder) is desired. The composition is to be initiated using benzalkonium chloride or butyrylcholine chloride. The components are divided into two elements. Element one contains the stabilized monomer and the plasticizer packaged in a glass vial or ampoule. Element two contains the components of thixotropic agent, radiopaque agent, and an amount of initiator to provide the desired setting time. The components of element two may be mixed together to form a homogeneously distributed powder (all components are solids), or the components may be added sequentially to the packaging container. The element two components are packaged into a syringe.

Experimentally it was discovered that ATBC degraded at the e-beam irradiation dose required for sterility. To prevent this degradation, element one components are sterilized using dry heat. Element two components are sterilized with an e-beam irradiation dose of approximately 25 kGy. Element two may or may not be placed into a foil pouch before e-beam irradiation. The two sterilization processes occur in parallel. Once both elements are sterilized, they are joined together into a pouch, which is sealed and is then exposed to ethylene oxide gas.

When it is time to use the composition, element one and element two are mixed. The polymerization time ("working time") is related to the initiator level. The flexibility of the resulting polymer is related to the amount of plasticizer.

The polymer created in example three can be similar to the polymer created in examples one and two. The plasticizer and initiator levels can be modified so the polymers are similar. Each plasticizer must be evaluated individually in the composition to give the desired amount of flexibility. One plasticizer may or may not be exchanged weight for weight in a composition. Once the plasticizer level is determined the initiator amount can be adjusted to give the desired polymerization time.

The result is a medical procedures kit that includes compositions 1 and 2, which are both sterilized and substantially retain their original properties in terms of viscosity and appearance. The compositions can be mixed and subsequently applied to a surface. Mixing of the compositions 1 and 2 initiates polymerization of the monomer, providing a polymer film or plug.

Example 4

Example two is repeated with acetyl tri-n-butyl citrate substituted for isopropyl myristate. The same sterilization sequence as described in example one is repeated. When element one and element two are mixed for their intended purpose, the polymerization time is undesirably extended and the resulting polymer does not have the desired physical characteristics.

While the invention has been described with reference to preferred embodiments, the invention is not limited to the specific examples given, and other embodiments and modifications can be made by those skilled in the art without departing from the spirit and scope of the invention.

While the invention has been described with reference to preferred embodiments, the invention is not limited to the specific examples given, and other embodiments and modifications can be made by those skilled in the art without departing from the spirit and scope of the invention.

What is claimed is:

1. A method for sterilizing an adhesive kit comprising:
   providing a first container containing at least a polymerizable monomer of a polymerizable adhesive composition which has not been sterilized;
   providing a second container containing at least one additional component of the polymerizable adhesive composition;
   subjecting the second container containing at least one additional component to a first sterilization process to reduce the bioburden on contents of said second container;
   combining the first unsterilized container and the second sterilized container in a kit packaging element; and
   subjecting the kit packaging element, containing the first unsterilized container and the second sterilized container, to a second sterilization process that terminally sterilizes contents of said first and second containers.

2. The method according to claim 1, wherein the first sterilization process does not terminally sterilize contents of said second container.

3. The method according to claim 1, wherein the first and second sterilization steps cause substantially no initiation of polymerization of the polymerizable adhesive composition.

4. The method according to claim 3, wherein the polymerizable adhesive is in the form of a liquid, gel or gel-like composition.

5. The method according to claim 1, wherein the at least one additional component is at least one of a plasticizer, a thickening agent, a radiopaque agent, and an initiator.

6. The method according to claim 1, wherein the at least one additional component is at least one of an initiator, a thickening agent, and a radiopaque agent.

7. The method according to claim 1, wherein the at least one additional component is an initiator.

8. The method according to claim 1, wherein the polymerizable monomer comprises a 1,1-disubstituted ethylene monomer.

9. The method according to claim 1, wherein the polymerizable monomer is an α-cyanoacrylate.

10. The method according to claim 1, wherein at least one of the first and second containers is sealed to maintain contents of said first container separate from contents of said second container.

11. The method according to claim 1, wherein at least one of the first and second containers is made of glass.

12. The method according to claim 1, wherein at least one of the first and second containers is made of plastic.

13. The method according to claim 1, wherein the first and second containers are independently selected from the group consisting of ampoules, vials, syringes, pipettes, tubes and applicators.

14. The method according to claim 1, wherein the first and second containers are compatible with e-beam.

15. The method according to claim 1, wherein the first container contains said polymerizable monomer, and said second container contains a plasticizer, a thickening agent, a radiopaque agent, and an initiator agent for said polymerizable monomer.

16. The method according to claim 1, wherein the first container contains said polymerizable monomer and at least one of a plasticizer, a thickening agent, and a radiopaque agent, and said second container contains an initiator agent for said polymerizable monomer and at least one other of the plasticizer, the thickening agent, and the radiopaque agent not packaged in the first container.

17. The method according to claim 1, further comprising sealing said kit packaging element prior to said second sterilization process.

18. The method according to claim 16, further comprising, prior to said sealing step, a third sterilization process to sterilize exposed surfaces in said kit packaging element.

19. The method according to claim 18, wherein said third sterilization process comprises exposure to ethylene oxide or hydrogen peroxide vapor.

20. The method according to claim 1, wherein at least one applicator for said polymerizable adhesive composition is included in said kit packaging element.

21. The method according to claim 1, wherein at least one material contained in said first container is incompatible with at least one material contained in said second container, at least prior to said first sterilization process.

22. The method according to claim 1, wherein at least one material contained in said first container is incompatible with at least one material contained in said second container, at least after said first sterilization process but not before said first sterilization process.

23. The method according to claim 1, wherein the first container is a glass ampoule and the second container is a plastic syringe.

24. The method according to claim 1, wherein the first and second sterilization processes are independently selected from the group consisting of irradiation, physical treatment, or chemical treatment.

25. The method according to claim 1, wherein the first sterilization process comprises e-beam irradiation at a dosage of from about 5-25 kGy.

26. The method according to claim 1, wherein the second sterilization process comprises e-beam irradiation at a dosage of from about 5-25 kGy.

27. The method according to claim 1, wherein at least one of said first sterilization process and said second sterilization process comprises dry heat.

28. The method according to claim 1, wherein said kit is sterilized to provide a Sterility Assurance Level of at least $10^{-3}$.

29. The method according to claim 1, wherein the second container contains at least one material that at least partially degrades during sterilization to become incompatible with the polymerizable monomer.

30. The method according to claim 29, wherein said at least one material that at least partially degrades is a plasticizer.

* * * * *